(12) United States Patent
Bi

(10) Patent No.: US 6,951,127 B1
(45) Date of Patent: Oct. 4, 2005

(54) DIGITAL VISCOMETER WITH NON CONTACT DISTANCE SENSOR

(75) Inventor: Hongfeng Bi, 800 W. Sam Houston Pkwy. S. #107, Houston, TX (US) 77042

(73) Assignee: Hongfeng Bi, Houston, TX (US)

( * ) Notice: Subject to any disclaimer, the term of this patent is extended or adjusted under 35 U.S.C. 154(b) by 0 days.

(21) Appl. No.: 10/403,702

(22) Filed: Mar. 31, 2003

(51) Int. Cl.⁷ .............................................. G01N 11/10
(52) U.S. Cl. ........................ 73/54.37; 73/23; 73/54.01; 73/54.33; 73/54.02; 73/54.23; 73/54.26; 73/54.27; 73/54.38; 73/54.28; 73/54.24; 73/54.25
(58) Field of Search ...................... 73/54.37, 23, 54.01, 73/54.33, 54.02, 54.23, 54.26, 54.27, 54.38, 73/54.28, 54.24, 54.25

(56) References Cited

U.S. PATENT DOCUMENTS

| | | | |
|---|---|---|---|
| 3,435,666 A | | 4/1969 | Fann |
| 3,500,677 A | * | 3/1970 | Broyles et al. ............. 73/54.37 |
| 4,062,225 A | * | 12/1977 | Murphy et al. ............. 73/54.35 |
| 4,175,425 A | | 11/1979 | Brookfield |
| 4,299,118 A | * | 11/1981 | Gau et al. ................... 73/54.35 |
| 4,571,988 A | * | 2/1986 | Murphy, Jr. ................ 73/54.33 |
| 4,668,911 A | * | 5/1987 | Mueller et al. ........ 324/207.18 |
| 4,765,180 A | * | 8/1988 | Clifton ....................... 73/54.33 |
| 5,167,143 A | * | 12/1992 | Brookfield ................... 73/54.23 |
| 5,365,777 A | * | 11/1994 | Layton ....................... 73/54.28 |
| 5,535,619 A | | 7/1996 | Brookfield |
| 5,763,766 A | | 6/1998 | Robinson |
| 5,777,212 A | * | 7/1998 | Sekiguchi et al. ......... 73/54.33 |
| 5,905,196 A | * | 5/1999 | Parshall ...................... 73/54.31 |
| 6,070,457 A | * | 6/2000 | Robinson ................... 73/54.33 |
| 6,167,752 B1 | * | 1/2001 | Raffer ....................... 73/54.28 |
| 2002/0007666 A1 | * | 1/2002 | Robinson ................... 73/54.28 |

\* cited by examiner

Primary Examiner—Hezron Williams
Assistant Examiner—André K. Jackson

(57) ABSTRACT

Viscometer (80) with a sample cup (42) rotatable by a pulley (26) and a timing belt (30) to shear a tested fluid thus imparting torque to a bob (44) mounted on a shaft (10) supported via a frictionless bearing (58), an optical distance sensor assembly (12) measures the distance to an arm (70) which is connected to the top of shaft (10). This distance information is further converted to the viscosity of the tested fluid.

18 Claims, 5 Drawing Sheets

Section A-A

DIGITAL VISCOMETER WITH NON CONTACT DISTANCE SENSOR

CROSS-REFERENCE TO RELATED APPLICATIONS

Not applicable.

BACKGROUND

1. Field of Invention

The present invention relates to measurement of viscosity with a frictionless spring, an arm and a non-contact distance sensor.

2. Description of Prior Art

A liquid between two surfaces will shear when one surface moves relative to the other. The force needed to make such a movement is directly related to the viscosity of the liquid (with the mechanical configuration factored out). Viscometers typically rotate a bob within a cylinder still with the liquid therebetween, or rotate an outer cylinder while keeping the inside coaxial bob inert. In such examples, torque is directly related to the viscosity of the liquid (again with mechanical configuration factored out).

Several types of arrangement have been applied to measure the torque due to the viscosity of the liquid. In U.S. Pat. No. 3,435,666, a helical spring is attached to the inside bob through a bob shaft while driving the outer cylinder. The shear force applied on the bob is proportional to the torque applied by the liquid, which is also measured by a strain gauge torque transducer. One of the drawbacks of this design is that the strain gauge torque transducer is located inside of the pressurized zone. Under elevated temperature and pressure conditions, if pressure is suddenly lost, hot sample could easily boil off and fill the pressurized zone. Thus strain gauge torque transducer would be easily contaminated and damaged by corrosive samples. Also, corrosive sample vapor can go up to the instrument top and damage the strain gauge torque transducer over time as well. Another drawback of this design is that two bearings are required to mount the bob and bob shaft assembly. Those bearings have drag force, which create extra error in the reading. Also, those bearings can be corroded easily under high temperature and corrosive sample vapors. Thus, traditionally it has been a major task to maintain those bob shaft bearings working properly for this type of viscometers. In U.S. Pat. No. 5,535,619, a torque tube is attached to the inside bob while driving the outer cylinder. The toque applied on the bob causes a rotational deflection on the readout wire, which is inside of the said torque tube. The readout wire is in turn mounted on a rigid jewel support located in the instrument head. An electromagnetic sensor pickup the rotations of the readout wire. One of the drawbacks of this design is that the torque tube and readout wire is structurally weak and excessive load can easily damage it. Another drawback of this design is that the lower end of the torque tube and readout wire is located in hot sample zone. High temperature can change the spring property of the torque tube and readout wire. This is the reason that this type of viscometer has poor accuracy and large zero drift at elevated sample temperatures.

It is an object of this invention to provide a viscometer that isolates its electronic torque sensor from corrosive samples and corrosive sample vapors.

It is an object of this invention to provide a reliable, rugged and temperature stable instrument with integrated electronics usable in viscosity measuring applications, under atmospheric, pressurized, low and high temperature conditions.

It is another object of this invention to provide a viscometer that operates with a wide range of liquids with viscoelasticity property measurement capability.

It is another object of this invention to provide a viscometer that eliminates measurement errors due to conventional bearing frictions.

It is another object of this invention to substantially reduce maintenance work yet meets industry standards of accuracy, reliability, durability, dependability, and ease of cleaning.

SUMMARY

A viscometer in accord with the present invention conveniently comprises a stationary frame from which a rotatable sample cup is suspended and includes a means for rotating the sample cup. Suspended within the sleeve is a bob capable of small angular motion about the longitudinal axis of the sample cup. The device is constructed so that the bob and the inside of the sample cup are immersed within the liquid, the viscosity of which is to be determined. The bob is suspended from the stationary frame by a resilient frictionless bearing, which permits limited angular motion about its center of rotation. With incremental torque applied on bob, this resilient frictionless bearing will increase its angular deflection. However the relationship between said torque and said angular deflection does not have to be linear. An arm is attached to the bob shaft or extended portion of the bob, and a non-contact distance sensor measures the movement of the arm. Given the known characteristics of the viscometer, the distance sensor output can be translated to the viscosity of the liquid.

One of the alternative embodiments of the present method is by replacing the said resilient frictionless bearing with a conventional helical or spiral torsion spring. And one or more conventional bearings would also be added for suspending said bob.

The apparatus and method of the present invention provide a fast response, bi-directional way to measure the shear stress property of fluid under shear condition.

DRAWING FIGURES

Other objects, features and advantages will be apparent from the following detailed description of preferred embodiments taken in conjunction with accompanying drawing in which:

FIG. 1 is a cross-section view of a preferred embodiment of the invention;

FIG. 2 is an isometric view of the top portion of the preferred embodiment with main shaft 56 hidden for clarity; FIG. 2A is an isometric view of the top portion of the alternative embodiment with a laser optical distance sensor; FIG. 2B is an isometric view of the top portion of the alternative embodiment with an eddy current non-contact distance sensor; FIG. 2C is an isometric view of the top portion of the alternative embodiment with a magnetic field sensor;

FIG. 3 is an isometric view of a resilient frictionless bearing with two sleeves; FIG. 3A is an end view of the frictionless bearing in FIG. 3; FIG. 3B is a cross-section view of the frictionless bearing in FIG. 3; FIG. 3C is a side view of the frictionless bearing in FIG. 3; FIG. 3D is a dissembled view of the frictionless bearing in FIG. 3;

Figure 1:
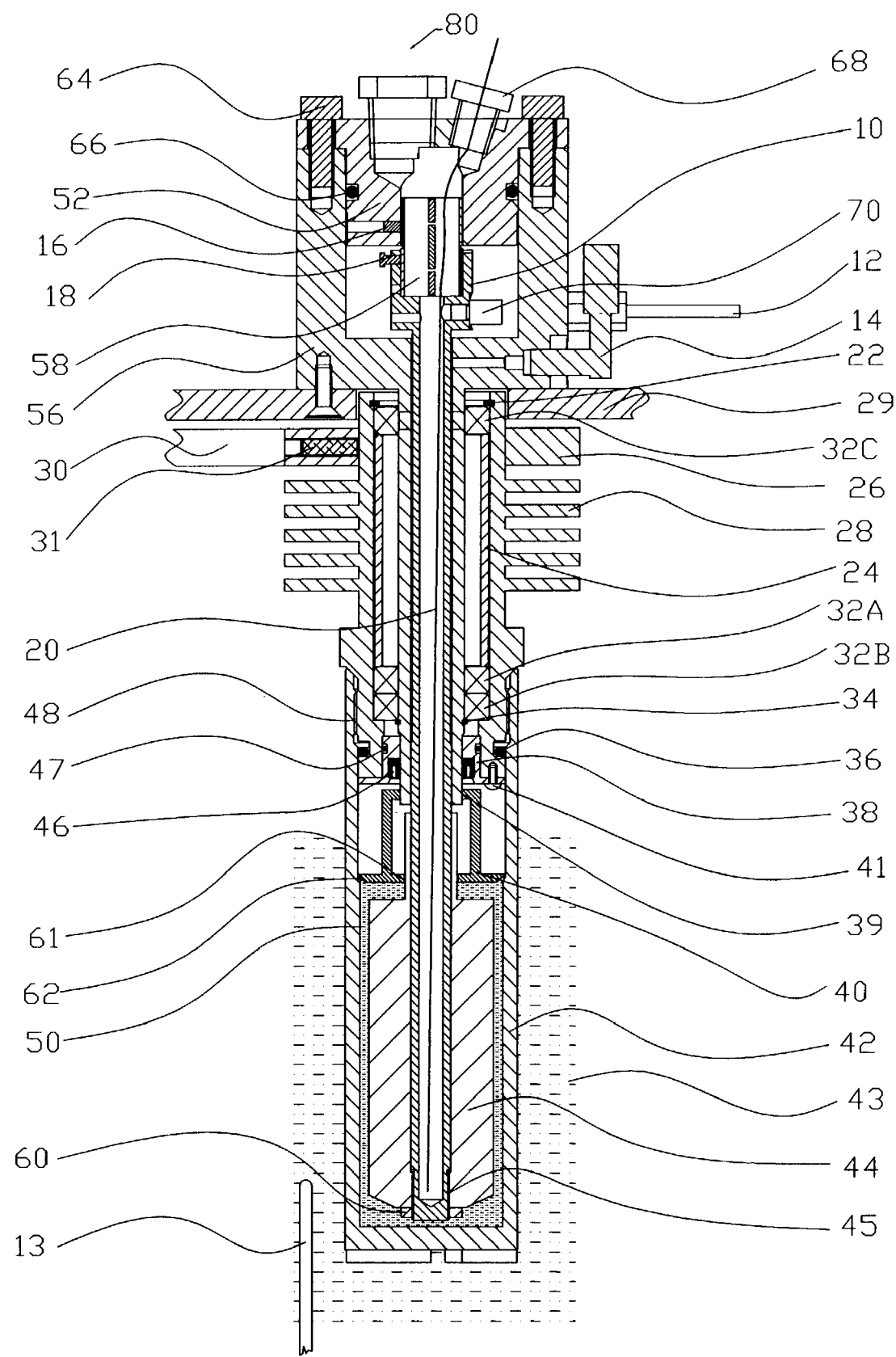

| Reference Numerals in Drawings | | | |
|---|---|---|---|
| 10 | bob shaft | 10A | bob shaft |
| 12 | fiberoptic displacement sensor assembly | 12A | fiberoptic displacement sensor assembly |
| 12a | laser optical distance sensor | 12b | eddy current non-contact distance sensor |
| 12c | magnetic field sensor | | |
| 13 | bath temperature probe | 13A | bath temperature probe |
| 14 | pressure port | 14A | pressure port |
| 16 | set-in screw | 18 | screw |
| 20 | thermal couple | 20A | thermal couple |
| 22 | snap ring | 22A | snap ring |
| 24 | spacer | 24A | spacer |
| 26 | pulley | | |
| 28 | rotor | 28A | rotor |
| 29 | support plate | 29A | support plate |
| 30 | timing belt | 31 | set-in screw |
| 32A | bearing | 32B | bearing |
| 32C | bearing | | |
| 34 | snap ring | 36 | o-ring |
| 38 | dynamic seal retainer | 39 | thread |
| 40 | anti-climber | 41 | screw |
| 42 | sample cup | 42A | sample cup |
| 43 | bath fluid | 43A | bath fluid |
| 44 | bob | 44A | bob |
| 45 | thread | 45A | thread |
| 46 | dynamic seal | 46A | dynamic seal |
| 47 | o-ring | | |
| 48 | thread | 48A | thread |
| 50 | sample | 50A | sample |
| 52 | cap | 52A | cap |
| 56 | main shaft | 56A | main shaft |
| 58 | frictionless bearing | 60 | lock nut |
| 61 | gap | 62 | gap |
| 64 | screw | 64A | screw |
| 66 | o-ring | 66A | o-ring |
| 68 | fitting | 68A | fitting |
| 70 | arm | 70A | arm |
| 70c | magnetized arm | | |
| 72A | leaf spring | 72B | leaf spring |
| 72C | leaf spring | | |
| 74 | stainless steel shell | | |
| 75 | stage stop | | |
| 76 | stainless steel shell | | |
| 78A | bearing | 78B | bearing |
| 80 | viscometer | | |
| 82A | bearing | 82B | bearing |
| 102 | expansion fitting | 104 | snap ring |
| 110A | fitting | 110B | fitting |
| 112 | helical spring | 114 | spring clamp |
| 120 | holder | 122 | cylindrical tub |
| 128A | o-ring | 128B | o-ring |
| 129 | water bath | 130 | Thread |
| 132 | tube | 134 | bearing shield |
| 200 | viscometer | | |

Description—FIGS. 1, 2, 3, 3A, 3B, 3C and 3D—Embodiment with Frictionless Bearing FIG. 1 is a cross-section view of a viscometer 80 with a bob 44 and a sample cup 42 with a sample liquid 50. Sample cup 42 is detachable from a rotor 28 via a screw thread 48. An o-ring 36 assures against gas escapes and/or escape of tested fluid through thread 48. Rotor 28 is mounted on a main shaft 56 through axially spaced bearings 32A, 32B, 32C with snap rings 22 and 34. Bearing 32A, 32B and 32C are needed for alignment, and spacer 24 is to keep bearings 32A, 32B and 32C in places. Sprocket 26 is secured to rotor 28 by a set-in screw 31. A motor-driven timing belt 30 transmits the power to turn sprocket 26. Main shaft 56 and a motor are mounted to support plate 29.

A cap 52 is tightened down to main shaft 56 with screw 64. An o-ring 66 prevents leakage between cap 52 and main shaft 56. Half of a frictionless bearing 58 is inserted into the inside bore of cap 52, and is secured with set-in screw 16. The other half of frictionless bearing 58 is secured to a bob shaft 10 with screw 18. Bob shaft 10 extends from top to the lower portion of sample cup 42. Bob shaft 10 does not have contact with the inside wall of main shaft 56. A bob 44 is coaxially supported from bob shaft 10 by thread 45. A lock nut 60 is screwed onto the bottom of bob shaft 10.

A dynamic seal retainer 38 is fixed to rotor 28 with a screw 41. A dynamic seal 46 prevents the leakage of gas when there is relative movement between main shaft 56 and dynamic seal retainer 38. An o-ring 47 prevents the leakage of gas between rotor 28 and dynamic seal retainer 38.

An anti-climber 40 is screwed on main shaft 56 through thread 39. Anti-climber 40 bottom edge has a small gap 62 with sample cup 42 inside wall, and there is a small gap 61 between inside wall of anti-climber 40 and outside wall of bob 44. This small gap 61 and 62 can keep sample 50 down at its measurement zone while preventing it climbing up.

A fitting 68 allows a thermal couple 20 going through while preventing the leakage of gas as well. Thermal couple 20 goes to the bottom of bob shaft 10 in order to get an accurate sample temperature reading. Nitrogen or pressurization media is applied through a fitting 14 to pressurize the whole pressure chamber.

Sample cup 42 is dipped into a bath fluid 43. A bath temperature probe 13 measures the temperature of bath fluid 43 in order to control its temperature.

Figure 2:
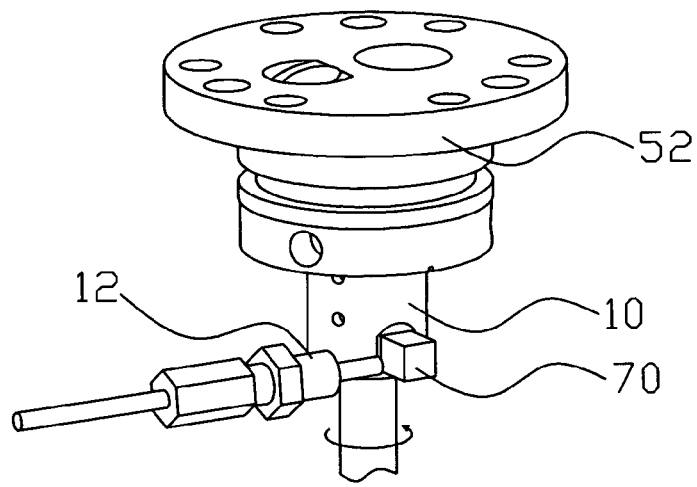

FIG. 2 is an isometric view of the top portion of viscometer 80 with main shaft 56 hidden for clarity. In FIG. 2, an arm 70 is screwed onto the side wall of bob shaft 10. A fiberoptic displacement sensor assembly 12 is mounted on the side wall of main shaft 56. Fiberoptic displacement sensor assembly 12 consists of a mounting fitting, a stainless steel tubing shield, a transparent sapphire window in front of the tubing shield and a bare fiberoptic displacement sensor inside of the tubing shield. The stainless steel tubing shield and the Sapphire window of fiberoptic displacement sensor assembly 12 separate the electronic and fragile portions of the sensor from pressurized zone, and prevent possible overload and corrosive damages to them as well.

Figure 3B:
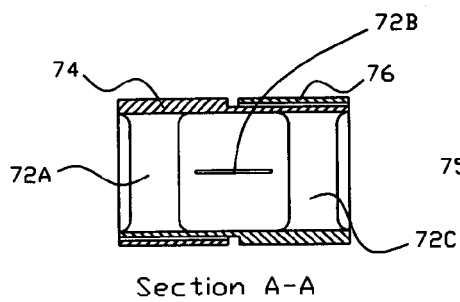
Figure 3A:
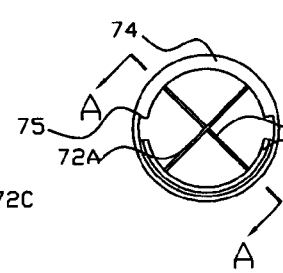
Figure 3C:
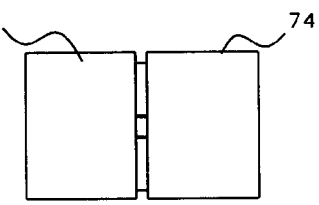
Figure 3:
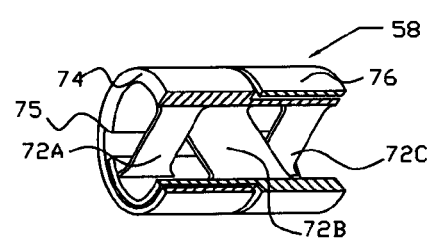
Figure 3D:
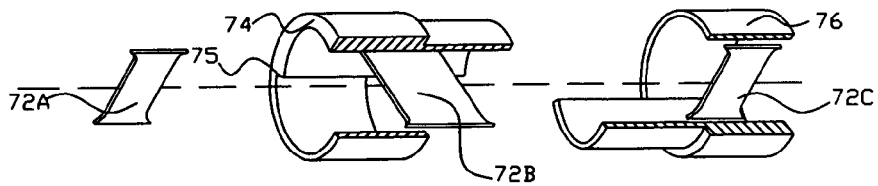
Figures 2A, 2B, 2C:
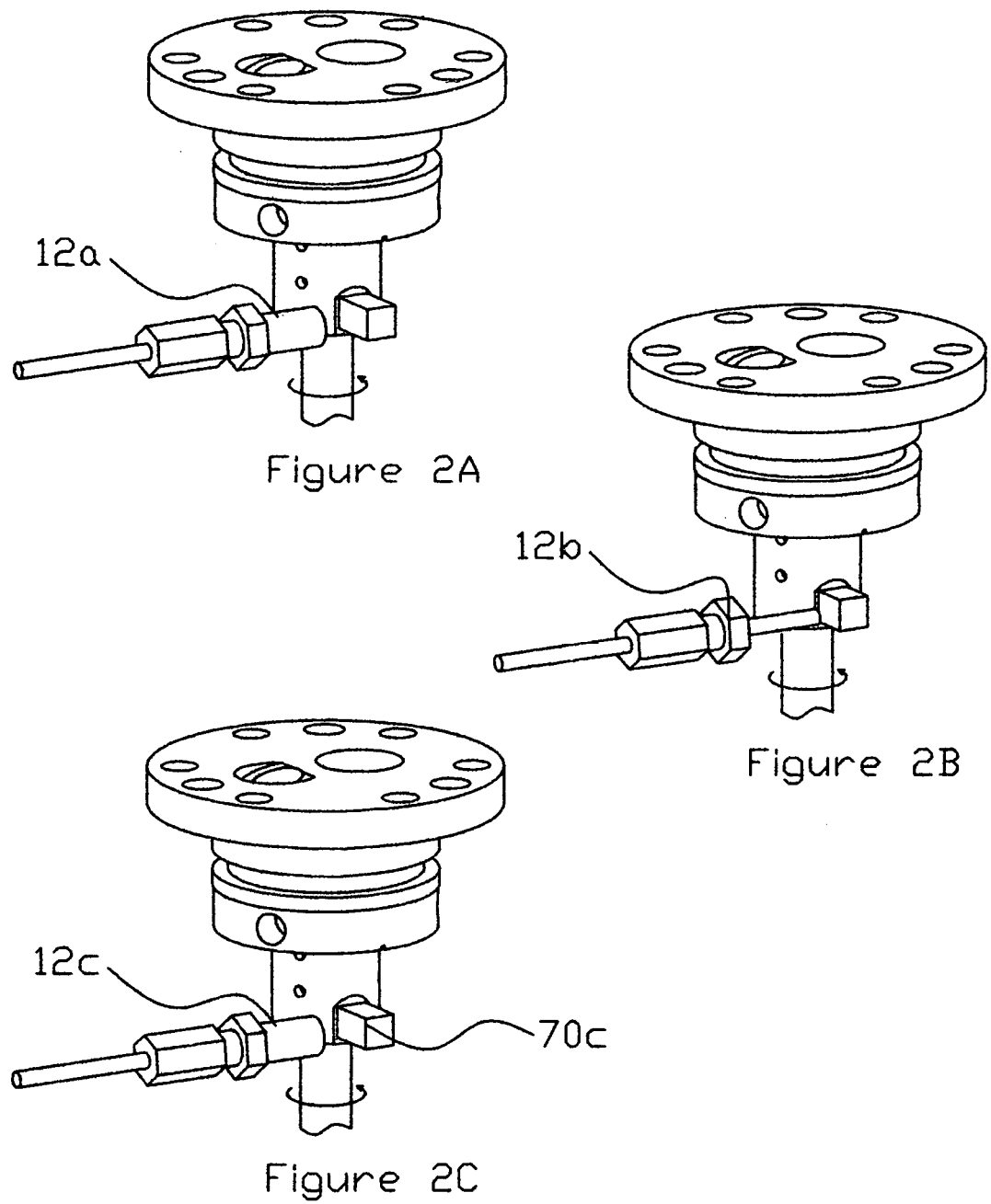

FIG. 3 shows an isometric view of a frictionless bearing 58 with two sleeves; FIG. 3A is an end view of the frictionless bearing in FIG. 3; FIG. 3B is a cross-section view of the frictionless bearing in FIG. 3; FIG. 3C is a side view of the frictionless bearing in FIG. 3; FIG. 3D is a dissembled view of the frictionless bearing in FIG. 3. Frictionless bearing 58 consists of two stainless steel shells 74 and 76 held in position by three leaf springs 72A, 72B and 72C on two perpendicular planes. As shown in FIG. 3D, both stainless steel shells 74 and 76 are consisting of an outside-smooth cylindrical portion and a smaller OD arc shell portion. The outside-smooth cylindrical portions of stainless steel shells 74 and 76 are disposed coaxially and have same OD. Each of the smaller arc shell portions of stainless steel shells 74 and 76 is inserted into the outside-smooth cylindrical portion of the other. Leaf springs 72A and 72C are disposed on one common plane while leaf spring 72B is in another. Leaf springs 72A, 72B and 72C all have their one end welded to stainless steel shell 74 while the other end welded to stainless steel shell 76. There is no direct contact between stainless steel shells 74 and 76—eliminating friction. Additionally, leaf springs 72A, 72B and 72C also provide the pivotal action corresponding to the common axis of stainless steel shells 74 and 76, which is inherently self-centering and requires no lubrication or maintenance. A stage stop 75 stops further relative movement between stainless steel shell 74 and stainless steel shell 76 when excessive torque load is applied on frictionless bearing 58.

Operation—FIGS. 1, 2 and 3—Embodiment with Frictionless Bearing

Figure 5:
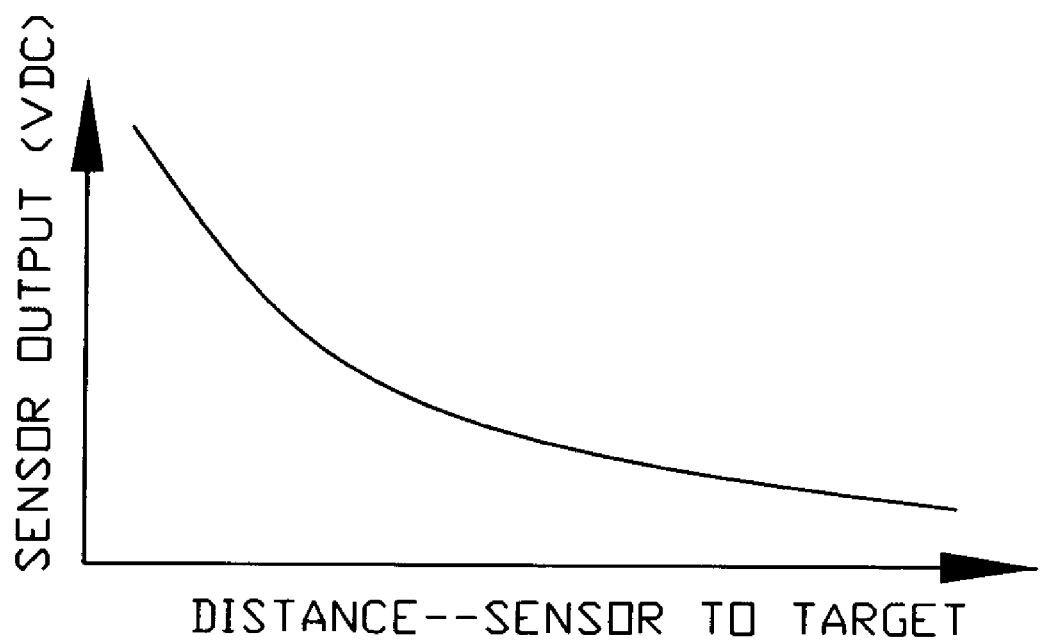
FIG. 5 is a typical non-contact distance sensor voltage output corresponding to distance.

During operation, a motor drives sprocket 26 rotating in counter clockwise direction viewing from the top of viscometer 80, through timing belt 30. Rotor 28 and sample cup 42 rotates together with pulley 26. Then a torque is applied to bob 44 due to the viscosity of sample 50. This torque is transferred to frictionless bearing 58 through bob shaft 10. This torque also causes a small counter clockwise direction deflection on frictionless bearing 58 as shown in FIG. 2. Arm 70 rotates with bob shaft 10, hence the distance between fiberoptic displacement sensor assembly 12 and arm 70 increases. The signal of fiberoptic displacement sensor assembly 12 is processed and collected thereafter. FIG. 5 shows dc voltage output vs. distance relationship for a typical fiberoptic distance sensor. As shown in FIG. 5, when distance is small, the slope of the curve is steep. Thus small distance change can cause large voltage output change. This ensures viscometer 80 has good resolution and accuracy when fluid shear stress applied on bob 44 is low. Meanwhile, when distance becomes larger, the slope of the curve becomes more leveled. Thus large distance can still be measured. This ensures viscometer 80 possesses wide measurement range.

Before operation, viscometer 80 need be calibrated. A series of different shear stress vs. sensor voltage output data are collected and a polynomial curve fitting is performed. Thus the non-linearity of sensor voltage output vs. shear stress is not a problem.

Additionally, frictionless bearing 58 is located on top where temperature is relatively low and constant. Therefore, elevated sample temperature does not affect the property of frictionless bearing 58. This ensures the temperature stability of viscometer 80.

Furthermore, there is an initial small gap between arm 70 and the tip of fiberoptic displacement sensor assembly 12 when fluid shear stress applied on bob 44 is zero. When sample cup 42 is driven to rotate in clockwise direction viewing from the top of viscometer 80, the distance between fiberoptic displacement sensor assembly 12 and arm 70 decreases. Therefor as long as fiberoptic displacement sensor assembly 12 and arm 70 do not contact, viscometer 80 can measure fluid shear stress applied on bob 44 no matter sample cup is rotating in clockwise or counter clockwise directions. So, this invention can measure visco-elasticity property of fluids when sample cup 42 is under dynamic vibrating movement.

Figure 6:
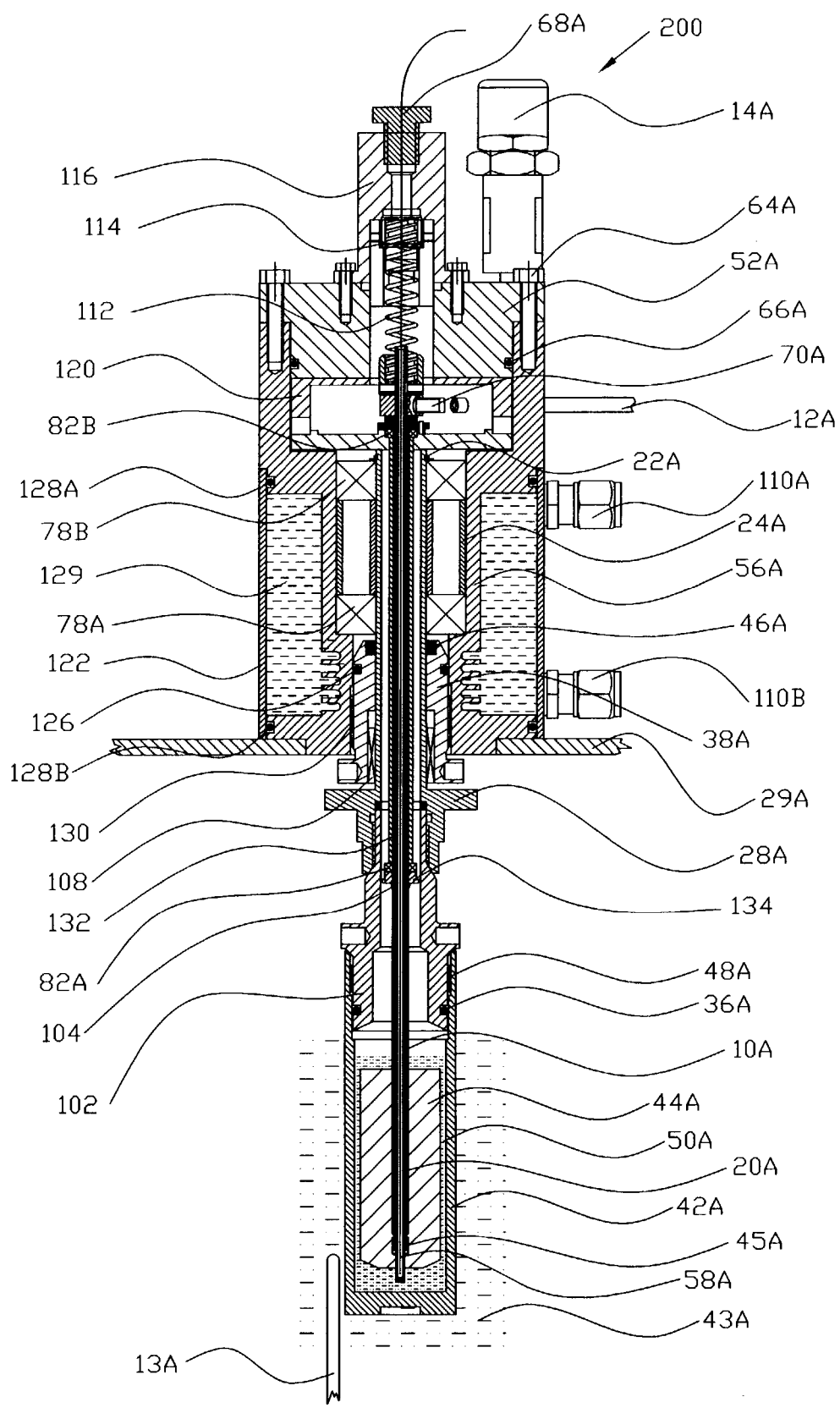
FIG. 6 is a cross-section view of an alternative embodiment with helical spring and bob shaft bearings.

Description—FIG. 6—Embodiment with Rotary Bob-Shaft Bearings

FIG. 6 is a cross-section view of a viscometer 200 with a bob 44A and a sample cup 42A with a sample liquid 50A. Sample cup 42A is detachable from an expansion fitting 102 via a screw thread 48A. An o-ring 36A assures against gas escapes and/or escape of tested fluid through thread 48A. Expansion fitting 102 in turn is detachable from a rotor 28A. Rotor 28A can be driven by a timing belt or a gear to rotate. Rotor 28A is mounted on a main shaft 56A through axially spaced bearings 78A, 78B with snap rings 22A. Bearing 78A and 78B are needed for alignment, and spacer 24A is to keep bearings 78A and 78B in places. Main shaft 56A and a motor are mounted to support plate 29A.

A cap 52A is tightened down to main shaft 56A with screw 64A. An o-ring 66A prevents leakage between cap 52A and main shaft 56A. A spring clamp 114 hold top portion of a helical spring 112. Spring clamp 114 is mounted on a spring holder 116. The bottom portion of helical spring 112 is fixed with bob shaft 10A. Bob shaft 10A extends from top to the lower portion of sample cup 42A. Bob shaft 10A is mounted on a holder 120 via axially spaced bearings 82A, 82B with snap rings 104 and a bearing shield 134. Holder 120 and a tube 132 are one integrated part and bearing shield 134 does not contact expansion fitting 102. There is a small gap between bob shaft 10A and tube 132 also. A bob 44A is coaxially supported from bob shaft 10A by thread 45A.

A dynamic seal retainer 38A is screwed onto main shaft 56A with a thread 130. A dynamic seal 46A prevents the leakage of gas when there is relative movement between main shaft 56A and dynamic seal retainer 38A.

An o-ring 128A, an o-ring 128B and a cylindrical tube 122 form a water bath 129. A fitting 110A and a fitting 1100B are through the wall of cylindrical tube 122 and fixed on cylindrical tube 122 as well. Fitting 110A and fitting 110B provide an inlet and outlet for circulation of water or other fluid to the bath.

A fitting 68A allows a thermal couple 20A going through while preventing the leakage of gas as well. Thermal couple 20A goes to the bottom of bob shaft 10A in order to get an accurate sample temperature reading. Nitrogen, or pressurization media is applied through a fitting 14A to pressurize the whole pressure chamber.

Sample cup 42A is dipped into a bath fluid 43A. A bath temperature probe 13A measures the temperature of bath fluid 43A in order to control its temperature.

An arm 70A is screwed onto the side wall of bob shaft 10A. A fiberoptic displacement sensor assembly 12A is mounted on the side wall of main shaft 56A. Fiberoptic displacement sensor assembly 12A consists of a mounting fitting, a stainless steel tubing shield, a transparent sapphire window in front of the tubing shield and a bare fiberoptic displacement sensor inside of the tubing shield. The stainless steel tubing shield and the Sapphire window of fiberoptic displacement sensor assembly 12A separate the electronic and fragile portions of the sensor from pressurized zone, and prevent possible overload and corrosive damages to it as well.

Operation—FIG. 6—Embodiment with Rotary Bob-Shaft Bearings

During operation, rotor 28A is driven to rotate through a timing belt, gear or other means. Sample cup 42A rotates together with rotor 28A. Then a torque is applied to bob 44A due to the viscosity of sample 50A. This torque is transferred to helical spring 112 through bob shaft 10A. This torque also causes a small rotational deflection on helical spring 112. Arm 70A rotates with bob shaft 10A, hence the distance between fiberoptic displacement sensor assembly 12A and arm 70A changes. The signal of fiberoptic displacement sensor assembly 12A is processed and collected thereafter. Because of the similar reasons discussed in viscometer 80, viscometer 200 has good resolution and accuracy when fluid shear stress applied on bob 44A is low and possesses wide measurement range as well.

Viscometer 200 can measure visco-elasticity property of fluids under dynamic vibrating movement of sample cup 42A as well.

RAMIFICATIONS

In preferred embodiment viscometer 80, arm 70 and fiberoptic displacement sensor assembly 12 can be replaced with a pair of concentrically mounted electrical stator and rotor to measure the rotation of bob shaft 10.

In preferred embodiment viscometer 80 and viscometer 200, fiberoptic displacement sensor assembly 12 can be replaced with any other kinds of non-contact sensors, which can sense the distance change of targets, such as eddy current effect sensors, hall effect sensors, magnetic field sensors, etc. Eddy current effect sensors and magnetic field sensors also possess similar voltage output vs. distance correlation as shown in FIG. 5. Additionally, arm 70 does not have to be square shaped or have to have a flat surface. Also, the vertical surface of Arm 70 facing fiberoptic displacement sensor assembly 12 does not have to be vertical either. It could be any angle corresponding to a horizontal plane. Finally, fiberoptic displacement sensor assembly 12 or other non-contact sensors do not have to be arranged approximately in the same plane that arm 70 rotates. Those sensors could be rearranged to have any angle comparing to the current position illustrated in FIG. 2. For example, fiberoptic displacement sensor assembly 12 could be rearranged vertically looking down at the top face of arm 70. Then modify the top face of arm 70 to have an inclined angle (for example 30-degree to horizontal plane). In this case, when arm 70 rotates, the vertical distance between fiberoptic displacement sensor assembly 12 and the top surface of arm 70 changes as well. This change of distance can be translated to viscosity information as well.

Viscometer 80 and viscometer 200 can also be reduced to much simpler construction for non-pressurized viscometer applications. It can be accomplished by removing scaling related components, such as all o-rings, dynamic seal retainers, etc. In non-pressurized application, sample cups can have open bottoms, and the lower part of sample cups can be immersed into a liquid the liquid's viscosity to be measured.

In viscometer 200, helical spring 12 can be removed. At the same time, make the tip of fiberoptic displacement sensor assembly 12A and arm 70A near side to have same magnetic pole. Thus they will be pushing each other. Rotate sample cup 42A in a direction so that shear stress on bob 44A would push arm 70A onto fiberoptic displacement sensor assembly 12A. Therefore the more shear stress is applied on bob 44A, the smaller the gap between fiberoptic displacement sensor assembly 12A and arm 70A. The signal of fiberoptic displacement sensor assembly 12A is processed and collected thereafter.

CONCLUSION, AND SCOPE

Accordingly, the reader will see that this invention can be used to construct a durable and economic electronic viscometer easily. The fast response and bi-directional measurement capability of this invention also makes sophisticated transient measurement of liquid property easy.

OBJECTS AND ADVANTAGES

From the description above, a number of advantages of my viscometer become evident:

(a) Very conveniently isolate the electronic portion of sensors from possible contamination or corrosion by sample.

(b) Due to the exponential output natural of most non-contact distance sensor, current invention covers very wide measurement range while maintaining excellent sensitivity and accuracy when measurement values are low.

(c) Very robust structure can handle extremely overload. Because sensor in this invention does not contact any moving parts, overload capacity is not limited by the load capacity of sensor.

(d) If high sensitive non-contact sensor is selected in current invention, torque induced rotational deflection can be designed very small. So the momentum of torsion assembly can be very small. Thus the response time of torque change can be very little.

(e) When non-contact sensors are used to measure bi-directional movement of arm, this invention can measure visco-elasticity of fluid under dynamic vibrating movement.

Further objects and advantages of my invention will become apparent from a consideration of the drawings and ensuing description.

What is claimed is:

1. Viscometer instrument comprising:
   (a) a rotor which is driven to rotate while contacting with a sample liquid to be measured,
   (b) means for driving said rotor to rotate,
   (c) a bob within said rotor,
   (d) means for suspending said bob therefor, said bob can rotate,
   (e) a member indirectly or directly connecting to a portion of said bob, and rotates together with said bob, and
   (f) means for sensing linear position of said member, and said means for sensing linear position has a characteristic of that when said means for sensing linear position is closer to said member, said means for sensing linear position output slope is steeper.

2. The instrument of claim 1 wherein means for sensing linear position of said member is a fiberoptic displacement sensor.

3. Viscometer instrument comprising:
   (a) a rotor which is driven to rotate while contacting with a sample liquid to be measured,
   (b) means for driving said rotor to rotate,
   (c) a bob within said rotor,
   (d) means for suspending said bob therefor, said bob can rotate,
   (e) a member indirectly or directly connecting to a portion of said bob, and rotates together with said bob, and
   (f) a laser optical distance sensor for sensing linear position of said member.

4. The instrument of claim 1 wherein means for sensing linear position of said member is an eddy current non-contact distance sensor.

5. The instrument of claim 1 wherein means for sensing linear position of said member is a magnetic field sensor.

6. The instrument of claim 1 wherein means for suspending said bob also has the character that with incremental torque applying on said bob, said bob has incremental rotational displacement.

7. The instrument of claim 6 wherein means for suspending said bob consists of a spring and a bob shaft which in turn mounted via bearing means.

8. The instrument of claim 6 wherein means for suspending said bob consists of a bob shaft, axially spaced bearing means that said bob shaft is mounted on, and a magnetic coupling consists of at least two separate magnets pushing each other in a non-contact manner while at least one of the said magnets is connected to or is part of said bob shaft.

9. The instrument of claim 1 wherein the rotor and the bob are mounted coaxially.

10. The instrument of claim 1 wherein said rotor and said bob are cylindrical shape.

11. The instrument of claim 7 wherein said rotor and said bob are cylindrical shape and are mounted coaxially.

12. The instrument of claim 1 wherein means for sensing linear position of said member-does not contact said member.

13. The instrument of claim 1 wherein means for sensing linear position of said member is arranged on the same plane that said member rotates.

14. The instrument of claim 1 wherein means for sensing linear position of said member is arranged on a different plane that said member rotates.

15. The instrument of claim 1 wherein means for suspending said bob consists of at least two sleeves held in position by leaf springs, at least one of said sleeves is mounted on a stationary frame, and at least one of the other sleeves directly or indirectly connecting to a portion of said bob, and rotates together with said bob.

16. The instrument of claim 15 wherein means for suspending said bob also has the character that with incremental torque applying on said bob, said bob has incremental rotational displacement.

17. The instrument of claim 16 wherein said rotor and said bob are cylindrical shape and are mounted coaxially.

18. The instrument of claim 17 wherein means for sensing linear position of said member is a fiberoptic displacement sensor.

* * * * *